United States Patent
Yang et al.

(10) Patent No.: US 12,215,139 B2
(45) Date of Patent: Feb. 4, 2025

(54) PREPARATION METHOD AND APPLICATION OF HIGH-PURITY PLANT-DERIVED RECOMBINANT HUMAN SERUM ALBUMIN

(71) Applicant: WUHAN HEALTHGEN BIOTECHNOLOGY CORP., Wuhan (CN)

(72) Inventors: Daichang Yang, Wuhan (CN); Quan Zhan, Wuhan (CN); Jiquan Ou, Wuhan (CN); Wenhui Yu, Wuhan (CN); Zhijie Qin, Wuhan (CN)

(73) Assignee: WUHAN HEALTHGEN BIOTECHNOLOGY CORP, Wuhan (CN)

( * ) Notice: Subject to any disclaimer, the term of this patent is extended or adjusted under 35 U.S.C. 154(b) by 0 days.

(21) Appl. No.: 18/518,227

(22) Filed: Nov. 22, 2023

(65) Prior Publication Data

US 2024/0262887 A1   Aug. 8, 2024

(51) Int. Cl.
| | |
|---|---|
| *C07K 14/765* | (2006.01) |
| *A61K 38/00* | (2006.01) |
| *A61K 45/06* | (2006.01) |
| *A61K 47/64* | (2017.01) |
| *A61P 3/00* | (2006.01) |
| *C07K 1/18* | (2006.01) |
| *C07K 1/20* | (2006.01) |

(52) U.S. Cl.
CPC ............ *C07K 14/765* (2013.01); *A61K 45/06* (2013.01); *A61K 47/643* (2017.08); *A61P 3/00* (2018.01); *C07K 1/18* (2013.01); *C07K 1/20* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,440,018 A | 8/1995 | Ohmura et al. | |
| 10,730,926 B2 * | 8/2020 | Yang | ............... C07K 14/765 |

FOREIGN PATENT DOCUMENTS

CN    102532254 B  *  6/2015  .......... B01J 20/3285

OTHER PUBLICATIONS

Anonymous "Monodisperse Chromatography Media" Product Guide, NanoMicro Tech. (Year: 2020).*
Chu et al. "High-throughput screening and optimization of mixed-mode resins for human serum albumin separation with microtiter filter plate" Biochemical Engineering Journal 131:47-57. (Year: 2017).*
First Office Action for Chinese Patent Application 2023101717190.
Second Office Action for Chinese Patent Application 2023101717190.
Chinese Office Action dated Jul. 6, 2023 for Chinese Application No. 202310171719.0.
Chinese Office Action dated Aug. 7, 2023 for Chinese Application No. 202310171719.0.

* cited by examiner

*Primary Examiner* — Sudhakar Katakam
*Assistant Examiner* — Zachary J Miknis
(74) *Attorney, Agent, or Firm* — Gregory P. Einhorn; Greer, Burns & Crain, Ltd.

(57) ABSTRACT

The present invention provides a method for preparing high-purity recombinant human serum albumin and its applications as a drug and biopharmaceutical excipient. The recombinant human serum albumin from *Oryza sativa* (OsrHSA) prepared by the present invention can be replaced of plasma-derived human serum albumin for uses of the clinic and pharmaceutical excipients in term of safe and effective. Furthermore, it can effectively maintain the biological activity of biological macromolecules.

14 Claims, 6 Drawing Sheets

FIG. 3

Table 1. Characteristics of Capto MMC

| | |
|---|---|
| Matrix | Highly cross-linked agarose, spherical |
| Ion exchange type | Multimodal weak cation exchanger |
| Ionic capacity | 0.07 to 0.09 mmol $H^+$/mL resin |
| Particle size, $d_{50v}$[1] | ~75 µm |
| Pressure/flow characteristics[2] | ≥ 600 cm/h at ≤ 0.3 MPa in a 1 m diameter column and 20 cm bed height (at 20°C using process buffers with the same viscosity as water)[3] |
| Dynamic binding capacity, $Q_{B10}$[4] | ≥ 45 mg BSA/mL resin at 30 mS/cm |
| pH stability, operational[5] | 3 to 12 |
| pH stability, CIP[6] | 3 to 14 |
| Working temperature[7] | 4°C to 30°C |
| Chemical stability | Stable to commonly used aqueous buffers, 1M acetic acid, 1.0 M $NaOH$[8], 8 M Urea, 6 M guanidine hydrochloride, 70% ethanol |
| Avoid | Oxidizing agents, cationic detergents |
| Autoclavability | 17 min at 121°C in 0.05 M phosphate buffer, pH 7, 10 cycles |
| Storage | 20 % ethanol, 4°C to 30°C |

[1] Median particle size of the cumulative volume distribution.

[2] For viscous buffers and samples the flow velocity must be optimized. Starting with a low flow velocity is recommended.

[3] The pressure/flow characteristics describes the relationship between pressure and flow under the set circumstances. The pressure given shall not be taken as the maximum pressure of the resin.

[4] Dynamic binding capacity at 10% breakthrough by frontal analysis at a mobile phase velocity of 300 cm/h in a Tricorn 5/100 column at 10 cm bed height (2 min residence time) for BSA in 50 mM sodium acetate, pH 4.75, 250 mM NaCl.

[5] pH range where resin can be operated without significant change in function.

[6] pH range where resin can be subjected to cleaning- or sanitization-in-place without significant change in function.

[7] Capto MMC can be used under cold-room conditions, but for some proteins the capacity may decrease.

[8] 1.0 M NaOH should only be used for cleaning purposes.

FIG. 4

2. Technical characteristics

| | |
|---|---|
| Appearance | White slurry, can be layered |
| Matrix | High rigidity agarose |
| Functional group | Complex weak cationic group |
| Average particle size | 75μm |
| Total ion capacity | 70-90μmol H+/mL resin |
| pH (neutral condition) +| > 28 mg BSA/mL packing gel(30mS/cm) |
| Max pressure | 0.5 MPa |
| Max flow rate | 1300cm/h (0.5MPa BXK 100/500, H=20cm,20℃) |
| Chemical stability | Stable in common aqueous buffers: 1M NaOH++++, 1M HAC++++, 6M GuHCl, 8M Urea, 70% ethanol, 30% isopropyl alcohol, 20% ethanol, 2% benzyl alcohol. Avoid contact with oxidizing agents, cationic detergents. |
| pH stability | 3-14(CIP),3-12(working) |
| Temperature tolerance | 2-40℃, Can't freeze. |
| Storage | 2-30℃, 20% ethanol |
| Recommended flow rate | 90-300cm/h |

+ Average particle sizes is the accumulated resin particle size of packing volume distribution ++ BXK5/100 columns with column height of 10cm, 10%BSA dynamic binding load under the condition of 50mM NaAc+ 0.25m NaCl pH 4.75 and flow rate of 2mL/min.

+++ This flow rate is a linear flow rate with BXK 100/500 20cm column height at 20℃ and pressure of 0.5MPa ++++ 1M NaOH and 1M HAc only be used for cleaning

FIG. 5

Description Characteristics Specification

Order information

| Product code | Product name | Package size |
|---|---|---|
| UniCAR-30S | 04021-030050 | |
| Uni<sup>a</sup>SP-30S | 04022-070050 | |
| UniDEAE<sup>a</sup>-30S | 04023-030050 | |
| UniQ<sup>a</sup>-30S | 04024-030050 | |
| UniQ<sup>xl</sup>-50XS | 04034-050030 | 30mL, 100mL, 400mL, 1L, 5L, 10L, 50L, ... 500L provided |
| UniCM<sup>a</sup>-50XS | 04021-050030 | |
| Uni<sup>a</sup>SP-50XS | 04022-050030 | |
| UniDEAE<sup>a</sup>-50XS | 04033-050030 | |
| Uni<sup>a</sup>HAM-50S | 04072-050050 | |
| Uni<sup>a</sup>HCM-50S | 04071-050050 | |
| Uni<sup>a,b</sup>MSP-10XS | 04012-030030 | |
| Uni<sup>a</sup>MSP-50XS | 04012-050030 | |

FIG. 6

Phenyl phase

| Product Name | UniHR Phenyl-30S | UniHR Phenyl-30L | UniHR Phenyl-60S | UniHR Phenyl-60L |
|---|---|---|---|---|
| Chromatography Technique | Hydrophobic interaction | Hydrophobic interaction | Hydrophobic interaction | Hydrophobic interaction |
| Matrix | Polymethacrylate | Polymethacrylate | Polymethacrylate | Polymethacrylate |
| Particle Size | 35 µm | 32 µm | 60 µm | 60 µm |
| Ligand | Phenyl | Phenyl | Phenyl | Phenyl |
| Dynamic Binding Capacity | ~30 mg·ml$^{-1}$ (Lys) | ~15 mg·ml$^{-1}$ (Lys) | ~20 mg·ml$^{-1}$ (Lys) | ~10 mg·ml$^{-1}$ (Lys) |
| Maximum Pressure | 1.0 MPa | 1.0 MPa | 0.8 MPa | 0.5 MPa |
| Clean in Place | 1 M NaOH / 70% Ethanol | 1 M NaOH / 70% Ethanol | 1 M NaOH / 70% Ethanol | 1 M NaOH / 70% Ethanol |
| Recommended Flow Velocity | 50-300 cm/h | 50-300 cm/h | 100-500 cm/h | 100-750 cm/h |
| pH Stability | 2-12 | 2-12 | 2-12 | 2-12 |
| Chemical Stability | Stable in commonly used buffers, 1 M HAc, 1 M NaOH, 1 M HCl, 70% ethanol, 30% isopropyl alcohol, 30% acetonitrile, 1% SDS, 6 M guanidine hydrochloride, 8 M urea, etc. Avoid long-term exposure to strong oxidant. | | | |
| Operational Temperature | 15-30 °C | 15-30 °C | 15-30 °C | 15-30 °C |
| Storage | 20% Ethanol, 4-25 °C | 20% Ethanol, 4-25 °C | 20% Ethanol, 4-25 °C | 20% Ethanol, 4-25 °C |

PREPARATION METHOD AND APPLICATION OF HIGH-PURITY PLANT-DERIVED RECOMBINANT HUMAN SERUM ALBUMIN

RELATED APPLICATIONS

This application claims the benefit of priority under 35 U.S.C. § 119(a) to China patent application No. 202310171719.0, filed on Feb. 27, 2023. The aforementioned application is expressly incorporated herein by reference in its entirety and for all purposes.

FIELD OF THE INVENTION

The invention belongs to the field of biotechnology, and in particular relates to a method for preparing a plant-derived recombinant human serum albumin.

BACKGROUND

Human serum albumin (HSA), also called human blood albumin, is a major protein component of blood or plasma, accounting for 45-55% of blood and 70~80% of plasma. Human serum albumin is a non-glycosylated protein consisting of 585 amino acids and has a molecular weight of about 66 kD. It is synthesized by the liver, and has an in vivo half-life of about 18-21 days in human, and synthesis rate in vivo of about 828 mg/kg/day. The concentration of HSA in the blood of adults is about 45 g/L. The main mechanism of HSA in human body is to increase blood volume and maintain plasma colloid osmotic pressure. The serum albumin concentration in health people is maintained within a certain range. It could lead to hypoalbuminemia when it is lower than the critical value of normal level (30 g/L). As result, it will cause various diseases, including cirrhotic ascites, severe sepsis, malignant ascites, intradialytic hypotension and other hypoalbuminemia-related diseases. In clinical practice, human serum albumin is widely used in the prevention and treatment for hemorrhagic trauma, shock caused by burns, increased intracranial pressure caused by cerebral oedema and injury, oedema or ascites caused by cirrhosis and nephropathy, hypoalbuminemia, and neonatal hyperbilirubinaemia, and for adjunctive treatment of cardiopulmonary bypass and burns, and for adjunctive treatment of haemodialysis and for the treatment of adult respiratory distress syndrome.

In 1943, E. J. Cohn, an American physical chemist, invented the fractionation with low temperature ethanol for the preparation of human serum albumin, which can obtain 29.9 g of albumin from 1 litre of plasma. This method has being used today since 1943. Its clinical application began during World War II, when it was used to rescue American military soldiers casualties in the battlefield to treat shock. It cannot meet the clinical demand in large quantities due to plasma shortage and also has the risk of transmitting prions such as human-derived viruses. The use of modern genetic engineering techniques to prepare human serum albumin instead of extracting it from plasma is imminent. Human serum albumin is used clinically in large doses (10 g-50 g/dose in single dose), and it is serious concern of the safety issues for recombinant human serum albumin technology, i.e., host cell protein contents should be below 1 ppm and endotoxin should be at or below 0.0083 EU/mg. Replacing HSA from plasma (pHSA) with recombinant human serum albumin (rHSA) requires not only high yield and purity, but also simple processes, easy scale-up (easy to reach several hundred tons capacity), cost-effective (production cost less than $2.0/g) and environment-friendly. Thus, the rHSA technology meet the challenges the purity, drug safety, the limit of scale-up and production cost of recombinant protein, which becomes a century hard nut to crack.

Since 1981, there have been extreme attempts to produce rHSA as an alternative from plasma using genetic engineering techniques. Numerous effords and attempts have been made using various hosts such as bacteria, yeast, animals and plants, however, it have not resulted in technological breakthroughs. The prokaryotic expression system, such as *E. coli*, was initially considered the most efficient expression platform in terms of its advantages of well-defined genetic information, faster growth rate, potential for expansion culture and high expression level. Due to the lack of mechanisms such as post-translational modification, rHAS aggregates to form inclusion bodies or is degraded due to abnormal cleavage of the signal peptide. As the consequence, rHSA expression level is extremely limited. Although the expression level of solubility of rHSA in *E. coli* has been improved by co-expression of folding enzymes and molecular chaperone, it is still in the lab-scale.

Animal cells can be used to express recombinant proteins with the same biochemical structure and modifications as human cells, which are widely used in the production of biopharmaceuticals, such as monoclonal antibodies and vaccines. Regarding to the huge market demand for human serum albumin in clinical applications, the animal system is the most ideal expression platform, however, it is challenges at the isolation and purification of recombinant proteins in downstream stream. Except for plasma system, such as animal mammary cells are also another important rHAS expression systems. In the early stage, the rHSA was expressed by transgenic mice. The expression level of rHSA was up to 11.9 g/L milk by optimizing the promoter etc. However, the total milk yield was limited the further application. In addition, rHSA has been successfully expressed in transgenic goats and dairy cows, while the difficulties in purification and high costs have prevented its clinical application.

Expression of rHSA in yeast also easily cause aggregation, and then the use of secretory yeast expression strategies can effectively avoid this phenomenon. A variety of yeast strains, such as *Saccharomyces cerevisiae, Hansenula polymorpha, Kluyveromyces lactis* and *Pichia pastoris*, are used to explore whether they can be used for large-scale production of rHSA. In order to improve the expression level of rHSA to gram level per liter, several approaches have been tested, including using the stronger promoter, signal peptide and intron sequences. Furthermore, the culturing process was optimized by combining cyclic/repeated fed-batch processes etc., which improve rHSA secretion efficiency and yields. Finally, the expression level of rHSA at 3 g/L level was achieved using *Saccharomyces cerevisiae* by Novozymes company in the UK, which further was successfully applied to pharmaceutical excipients. Mitsubishi Tanabe Pharma in Japan produced rHSA at 10 g/L levels through using *Pichia pastoris* expression system and the study results of rHSA the clinical trial was published in 1997, and then was approved by the PMDA in 2007. Unfortunately, it was withdrawn from the market in 2009.

Plant cells have the similar post-translational modification mechanism over that of animal cells, with the advantages of the characteristics of high yield, cost-effective and human pathogen-free. Therefore, the use of plant cell as expression system for rHSA production is very promising. Tobacco and potato were firstly used to express rHSA, however, its yield is very low. The production of rHSA using rice suspension cells and tobacco BY-2 cells has also been reported. The yield and production cost are still problematic. Cereal grain is a organ for protein synthesis and storage. In 2011, H E et al. reported that large scale production of the rHSA in transgenic rice grain. The OsrHSA (recombinant human serum albumin from Oryza sativa, OsrHSA) yields reached 10.58% of the total soluble protein using endosperm-specific promoters, endomembrane-directed storage and codon optimization strategies, which is 20-folds higher that of exceeding the minimum commercial yield requirement. The primary and secondary and tertary structures of the OsrHSA were equivalent to the plasma-derived human serum albumin (pHSA).

Human serum albumin has 3 binding sites that are the reversibly binding small molecules. Therefore, rHSA can bind small molecules such as endotoxin non-specifically during the purification of rHSA. It is extremely difficulty to remove the endotoxin from OsrHSA to meet the endotoxin content criteria of Chinese Pharmacopoeia and the US Pharmacopoeia (Chen et al. Human serum albumin from recombinant DNA technology: Challenges and strategies. BBA, 2013, 1830 (12): 5515-5525).

In addition, safety is critical to drug's druggability. The safety of OsrHSA is even more challenging. First, the dosage of human serum albumin is up to 10-50 g/dose, which is 50-100 times higher than that of monoclonal antibody drugs (0.2-0.5 g), which its purity is required as much high as possible. Secondly, it is a challenge to decrease the contents of residual host protein (HCP) in drug product as low as possible. Bio-macromolecules have extremely complex structures, and the main difference from chemical drugs is immunogenicity. Thus, the residual HCP content is a critical control parameter (CCP) for the safety of OsrHSA. According to ICH, the HCP content of recombinant protein drug is ranges from between about 1 to about 100 ppm, which specifically mainly depends on the dosage of the drug. The higher the dosage, and the lower the HCP content is required. According to the dose of 10-50 grams of OsrHSA in clinic, the residual host cell protein contents of OsrHSA should be less than 10 ppm. Simultaneously, the residual host cell protein should be low immunogenicity. Higher purity of rHSA can be required more purification steps to remove HCP to meet the purity requirements. However, the increase of purification steps not only decreases the recovery rate, but also increases the cost and transfer the cost to the drug cost. Therefore, rHSA with low cost is challenge to rHSA. It is significance to develop a simple process of rHSA with low endotoxin, lower HCP content and high recovery rate to meet the requirements of clinical grade rHSA.

CN103880947B discloses a chromatographic method for isolating and purifying high-purity recombinant human serum albumin, mainly introducing a washing step with isopropyl alcohol in the second chromatography step, which greatly reduces the endotoxin level compared to the previous preparation method. Patents U.S. Pat. Nos. 8,609,416, 10,618,951 and U.S. Ser. No. 11/492,389 B1 can only control the endotoxin level below 1 EU/mg, while the Chinese Pharmacopoeia and the US Pharmacopoeia require the endotoxin level in human serum albumin to be below 0.0083 EU/mg. Once the endotoxin is higher than this level, a febrile reaction in human will be produced, and may cause serious safety problems. The more lower the endotoxin content in OsrHSA will benefit more safety fro human. It is extreme challenge to control endotoxin contents in rHSA below to the requirement of the Chinese Pharmacopoeia and the US Pharmacopoeia.

SUMMARY

An object of the present invention is to provide a method for preparing high-purity OsrHSA.

Another object of the present invention is to provide a OsrHSA prepared by the method.

Yet another object of the present invention is to provide uses of OsrHSA.

According to one aspect of the present invention, a method for preparing high-purity OsrHSA comprises the steps of:
1) preparing a crude extract of OsrHSA;
2) subjecting the crude extract of OsrHSA to primary purification by cation exchange chromatography (A), adding a wash steps with isopropanol to remove endotoxin and to obtain a primary product I;
the buffer comprises washing buffer, equilibration buffer I and equilibration buffer II; wherein the washing buffer comprises 10-20% absolute isopropanol by volume, the equilibration buffer I comprises 0-10% absolute isopropanol by volume, and the equilibration buffer II comprises 5-15% absolute isopropanol by volume; the cation exchange chromatography comprises a composite resin of CAPTO-MMC™ or BESTAROSE DIAMOND MMC™;
3) subjecting the primary product I to anion exchange chromatography B, to obtain an intermediate product II;
the anion exchange chromatography B comprises a composite resin of UNIHAM-50S, which is a matrix having large pore size and high flow rate; the processing parameters for the chromatography on UNIHAM-50S™ comprises loading solution: pH 8.0, conductivity 1~5 mS/cm;
washing buffer: pH 8.0, conductivity 9~9.5 mS/cm;
elution buffer: pH 8.0, conductivity 40-47 mS/cm;
4) subjecting the intermediate product II to hydrophobic chromatography C, to obtain the high-purity OsrHSA;
the hydrophobic chromatography comprises a rigid matrix hydrophobic resin of UNIHR PHENYL 80L™, UNIHR PHENYL 60S™ or UNIHR PHENYL 30L™, and UNIHR PHENYL 30L™ is optimal.

In alternative embodiments of methods as provided herein, wherein in the step 3), the elution buffer for UNIHAM-50S™ has a conductivity of 40~47 mS/cm, and preferably 42 mS/cm.

In alternative embodiments of methods as provided herein, wherein in the step 4), the elution buffer for the chromatography has a conductivity of 80~92 mS/cm, preferably 84 mS/cm.

In alternative embodiments of methods as provided herein, the high-purity OsrHSA is prepared by the following steps comprise of:
1a) preparing a crude extract of composite;
2a) subjecting the crude extract of OsrHSA to cation exchange chromatography A, adding isopropanol into a washing buffer to remove endotoxin, to obtain a primary product I; adding pure water and a protective agent and then adjust pH to 8.0 and conductivity to 5.4 mS/cm, then filtration;
3a) subjecting the primary product I to anion exchange chromatography B to obtain an intermediate product II; filling UNIHAM-50S™ resin into a chromatography column with a diameter of >45 cm with a height of 48.8-52 cm, and performing chromatography at a flow rate of 400~600 L/h.

the buffer used for the chromatographies sequentially comprises of:

The equilibration buffer: 10~20 mM PB, pH 7.9~8.1, cond 1~3 mS/cm;

The re-equilibration buffer: the same as the equilibrium solution above;

The washing buffer: 10~20 mM PB, 150~170 mM NaCl, pH 7.9~8.1, cond 9~9.5 mS/cm;

The elution buffer: 10~20 mM PB, 420~460 mM NaCl, pH 7.9~8.1, cond 41~43 mS/cm;

4a) subjecting the intermediate product II to hydrophobic chromatography C, to obtain the high-purity OsrHSA;

Wherein ammonium sulfate is added to the eluate of the intermediate product II collected from the chromatography of the step 3a) to prepare a stock solution with pH of 6.6 and the conductivity of 86 mS/cm, which is used for loading to chromatography C with UniHR Phenyl 30L after filtration.

The UniHR Phenyl resin was loaded onto >30 cm diameter column with a loading height of >45 cm, and the chromatography C was performed at a flow rate of 70~80 L/h, and the equilibrium buffer for the chromatography C comprises 10~20 mM PB, 500~600 mM $(NH_4)_2SO_4$, 2 g/L sodium octanoate, pH 6.5-6.6.

According to the another aspect of the present invention, the high-purity OsrHSA produced by the method of the present invention has the following characteristics comprising of:

Protein purity greater than (>) 99.9999%;
Residual host cell proteins less than (<) 1 µg/g protein.
Residual host cell DNAs <0.5 ng/g protein; and
Endotoxin contents <0.0083 EU/mg.

The high-purity OsrHSA prepared by the method of the present invention is safety and tolerable when it intravenously injects into human beings, does not produce anti-host cell protein or anti-drug antibodies (ADA) and the efficacy is non-inferiority to the plasma-derived human serum albumin (pHSA).

According to another aspect of the present invention, there is provided a pharmaceutical composition comprising OsrHSA of the present invention. The OsrHSA of the present invention can be used to pharmaceutically or physiologically acceptable excipients as a pharmaceutical composition suitable for clinical use.

According to another aspect of the present invention, the recombinant human albumin of the present invention could be used as a lyophilized protectant and/or excipient application of protein drugs.

The present invention has the advantageous benefits that:

1. The present invention provides a process for preparing high-purity OsrHSA that meets the needs of clinical applications.

2. This invention solves the safety issue of rHSA due to high dose intravenous injection, which is beseted for more than 40 years. It breaks through the key core technology of preparing high purity of rHSA, i.e. purity >99.9999%, host cell protein (HCP) content is less than 1 µg/g; residual host cell DNAs is less than 0.5 ng/g).

3. The present invention solves the dilemma that endotoxin is not easily removed due to the binding small molecules characteristics of human serum albumin, which the endotoxin content of rHSA for clinical applications required as low as 0.0083 EU/mg protein to meet the US FDA and Chinese Pharmacopoeia, and to solve the safety problem that produce fever in the body when higher endotoxin.

Because of the above advantages, the OsrHSA prepared by the present invention is safe and efficacy. In addition, the OsrHSA prepared by the method of the present invention can be used in clinic use and pharmaceutical excipients to replace of pHSA, which effectively protect the biological activity of biopharmaceuticals.

In alternative embodiments, provided are methods for preparing high-purity recombinant human serum albumin from *Oryza sativa* (OsrHSA), comprising the following steps of:

(a) preparing a crude or unpurified extract of OsrHSA;

(b) subjecting the crude extract of OsrHSA to cation exchange chromatography (A) comprising a cation exchange column, whereby OsrHSA binds to the cation exchange column, (c) adding isopropanol into a first buffer to remove endotoxin to obtain a primary product I;

wherein the first buffer comprises: a washing buffer, an equilibration buffer I and an equilibration buffer II;

wherein first the washing buffer comprises between about 10-20% absolute isopropanol by volume, the equilibration buffer I comprises between about 0-10% absolute isopropanol by volume, and the equilibration buffer II comprises between about 5-15% absolute isopropanol by volume, (d) washing the cation exchange column with the washing buffer, then washing the column with equilibration buffer I, then washing the column with equilibration buffer II, (e) eluting OsrHSA from the cation exchange chromatography, thereby obtaining a primary product I;

wherein the cation exchange chromatography comprises a cationic/hydrophobic composite resin;

(f) subjecting the primary product I to anion exchange chromatography B comprising an anion exchange column, to obtain an intermediate product II;

wherein the anion exchange chromatography (B) comprises a composite resin-comprising a matrix having large pore size and high flow rate;

and the parameters of the anion exchange chromatography comprise:

(i) adding or loading onto to the anion exchange column a loading sample under conditions comprising: pH 8.0, conductivity between about 1 to 5 mS/cm;

(ii) adding or loading onto to the anion exchange column a washing buffer under conditions comprising: pH 8.0, conductivity between about 9 to 9.5 mS/cm;

(iii) adding or loading onto to the anion exchange column an elution buffer comprising: pH 8.0, conductivity between about 30 to 50 mS/cm;

thereby eluting off the anion exchange column the intermediate product II; and (g) subjecting the intermediate product II to hydrophobic chromatography (C) comprising a hydrophobic column to obtain the high-purity OsrHSA, wherein the hydrophobic column is washed by loading a washing buffer onto the hydrophobic column, and an eluting buffer is loaded onto the hydrophobic column, thereby generating the high-purity OsrHSA, and the hydrophobic chromatography comprises a rigid, hydrophobic resin.

In alternative embodiments of methods as provided herein:

the OsrHSA is expressed in rice seed;

the elution buffer in the step (f) has a conductivity of between about 40 mS/cm and 47 mS/cm, or about 42 mS/cm;

the hydrophobic chromatography resin in the step (g) comprise highly crosslinked polymethacrylate beads of uniformed particle size and open pore structure, and the particle size is about 35 μm, the pore size is about 500 μm, the dynamic binding capacity is about 30 mg/ml (Lys), the operating pressure is less than about 0.8M Pa, the operating has a pH range of about pH 2 to pH 12;

the elution conductivity of the chromatography in the step (g) is between about 80-92 mS/cm;

the elution conductivity of the chromatography in the step (g) is between about 75 to 90 mS/cm, between about 80 to 87 mS/cm, or about 84 mS/cm;

the chromatography in step (f) comprises use of the following buffers:

an equilibration buffer comprising: between about 10 to 20 mM phosphate buffer (PB), between about 7.9 to 8.1 pH, conductivity between about 1 to 3 mS/cm; a re-equilibration buffer: the same as the equilibration buffer;

a washing buffer: between about 10 to 20 mM PB, between about 150 to 170 mM NaCl, between about 7.9 to 8.1 pH 7.9~8.1, between about 9 to 9.5 mS/cm conductivity;

an elution buffer comprising: between about 10 to 20 mM PB, between about 420 to 460 mM NaCl, between about pH 7.9 to 8.1, between about 41 to 43 mS/cm conductivity; and/or and a chromatography buffer used in step (g) comprises: between about 10 to 20 mM PB, between about 500 to 600 mM $(NH_4)_2SO_4$, between about 1 and 3 g/L, or about 2 g/L sodium octanoate, between about pH 6.5 to 6.6.

In alternative embodiments, provided are high-purity OsrHSA prepared according to a method as provided herein, wherein the OsrHSA has the following characteristics or properties:

a purity of greater than 99.9999%;
residual host cell proteins less than 1 μg/g protein;
residual host cell DNAs less than 0.5 ng/g protein; or
endotoxin contents less than 0.0083 EU/mg.

In alternative embodiments, provided are drug compositions comprising a high-purity OsrHSA as provided herein.

In alternative embodiments, provided are methods for treating hypoalbuminemia comprising administering to an individual in need thereof a high-purity OsrHSA as provided herein.

In alternative embodiments, provided are excipients of biopharmaceutical drugs comprising the high-purity OsrHSA as provided herein.

In alternative embodiments, provided are freeze-drying protectants comprising the high-purity OsrHSA as provided herein.

In alternative embodiments, provided are excipients for a biopharmaceutical drug comprising a high-purity OsrHSA made by a method as provided herein.

In alternative embodiments, provided are freeze-drying protectants comprising a high-purity OsrHSA made by a method as provided herein.

In alternative embodiments, provided are drug formulations comprising: an excipient comprising a high-purity OsrHSA made by a method as provided herein, and an active drug agent.

In alternative embodiments, provided are products of manufacture comprising a freeze-drying protectant comprising a high-purity OsrHSA made by a method as provided herein.

In alternative embodiments, the OsrHSA has the following characteristics or properties:

a purity of greater than 99.9999%;
residual host cell proteins less than 1 μg/g protein;
residual host cell DNAs less than 0.5 ng/g protein; and
endotoxin contents less than 0.0083 EU/mg.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference in their entireties for all purposes.

DESCRIPTION OF THE DRAWINGS

FIG. 3 illustrates a table showing characteristics of CAPTO-MMC™ FIG. 4 illustrates a table showing characteristics of BESTA-ROSE DIAMOND MMC™ FIG. 5 illustrates a table showing that UNIHAM-50S™ or any of the resins described in the table of FIG. 4 can be used in practicing methods as provided herein.

FIG. 6 illustrates a table showing characteristics of UniHR PHENYL 60S™, UNIHR PHENYL 30L™, UNIHR PHENYL 80L™.

Figure 1:
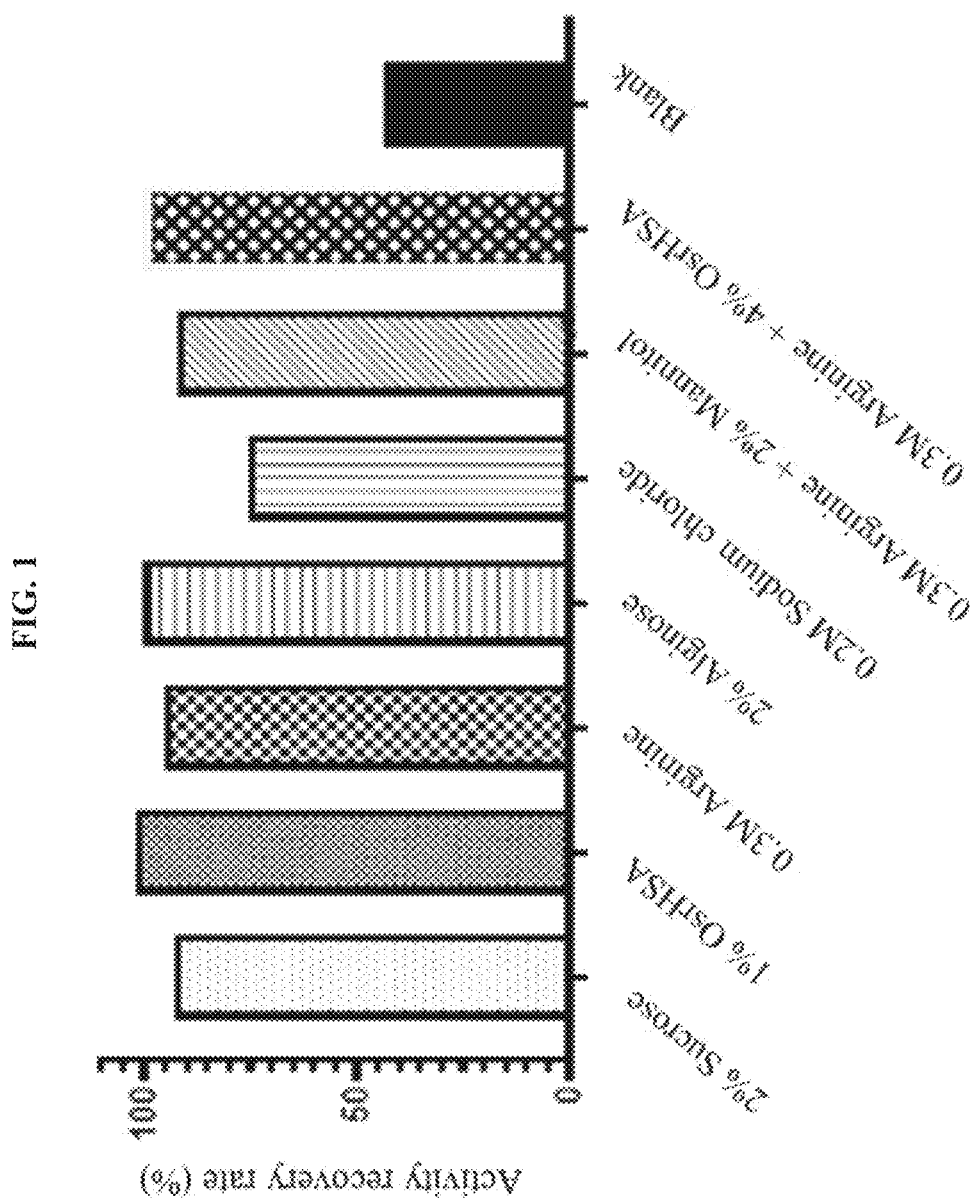
FIG. 1 graphically illustrates data showing the effect of different protectants on the activity of OsrPA after freeze-drying.

The drawings set forth herein are illustrative of exemplary embodiments provided herein and are not meant to limit the scope of the invention as encompassed by the claims.

DETAILED DESCRIPTION

The characteristics and advantages of the present invention can be further understood by the following detailed description in conjunction with the accompanying drawings. The embodiments provided are merely illustrative of the method of the present invention and do not in any way limit the rest of what is disclosed by the invention.

The reagents and instruments used in the following examples are common commercially available, unless otherwise stated.

Preparation of OsrHSA:

Transgenic rice containing OsrHSA was prepared referring to the method of Chinese patent No. 200510019084.4;

OsrHSA was extracted from rice seeds to obtain a clear OsrHSA extract referring to the method of Chinese patent No. 201010606635.8, U.S. Pat. No. 9,255, 138B2 and U.S. Ser. No. 10/183,984B2.

The cation exchange chromatography A was performed referring to the method of Chinese patent CN103880947B.

Exemplary Resins

In alternative embodiments, CAPTO-MMC™ is the commercial product bought from Cytiva, having characteristics as set forth the table illustrated in FIG. 3.

CAPTO-MMC™ is a salt tolerant multimodal weak cation exchanger. Compared with traditional ion exchangers, it has different selectivity: it is a multimodal cation exchangers with different selectivities compared to conventional ion exchangers; has high dynamic binding capacity at high conductivity increases productivity; high volumetric throughput reduces processing time; has a smaller unit operations allow for cost-effective processing and reduced investment; and its fillers meet industry needs for security of supply, consistent performance, and regulatory support.

In alternative embodiments, BESTAROSE DIAMOND MMC™ is the commercial product bought from Bestchrom (Shanghai) Biosciences Co., Ltd., having characteristics as set forth the table illustrated in FIG. 4.

UNIHAM-50S™ is the commercial products from Suzhou NanoMicro Technology Co, Ltd., which can be bought by the public. UNIHAM-50S™ or any of the resins described in the table of FIG. 5 can be used in practicing methods as provided herein.

In alternative embodiments, UNI®HAM/HCM™ have the following characteristics:

| UNI ®HAM/HCM ™ serials | |
| --- | --- |
| Mechanism | ion exchange |
| Matrix | Monodisperse polyacrylate |
| Dynamic binding capacity | |
| Pore size | |
| Particle size | Approximately 60 μm |
| Purification | Capture, intermediate purification |
| Main characteristics | Surface modification of hydrophilic membrane layer, low nonspecific adsorption, special design of particle size and space, high loading and special selectivity. |
| Classical application | Special design, providing more choices |

In alternative embodiments, UNIHR PHENYL 60S™、UNIHR PHENYL 30L™、UNIHR PHENYL 80L™ are commercial products bought from Suzhou NanoMicro Technology Co, Ltd., having characteristics as illustrated in FIG. 6.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About (use of the term "about") can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 75%, 80%, 85%, 90%, 91%, 92%, 93%, 94%, 95%, 96%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be understood that the invention is not limited to such examples.

EXAMPLES

Example 1: Preparation of OsrHSA with High Purity, Low Endotoxin and Low HCP Content CN103880947B discloses a chromatography method for isolating and purifying high-purity recombinant human serum albumin (hereinafter referred to as the old process), the main steps comprise of: the HSA-expressing rice grains were dehulled, polished and mechanically crushed into 180-200 mesh rice flour; the rice flour was extracted for 1~3 hours with the ratio of rice flour: extraction buffer of 1:5, adjusted to pH 4.5 using 20% acetic acid, followed by acid precipitation for 3-12 hours. And then solid-liquid separation is obtained through a plate and frame filter press. The crude extracts containing OsrHSA was subjected to complite cation chromatography, complite anion chromatography and hydrophobic chromatography, Phenyl HP, followed by ultrafiltration and concentration to obtain >200 mg/ml drug solution of OsrHSA. The method involved a washing step with isopropanol in the second chromatography step.

In the old process, the resins for the isolation and purification comprises a highly cross-linked rigid agarose matrix. This resin has disadvantages of low pressure tolerance, slow flow rate and weak ability to remove impurities and endotoxins. It needs the better resins that have the ability to overcome the disadvantages of the resins with agarose matrix. With the development of resin preparation processes, poly(methacrylate) rigid matrix have the advantages of higher pressure resistance, faster flow rates, better impurity removal, and higher product quality compared to the resin with agarose matrix. A present process has been developed using the new resins with rigid matrix, so that the rersin height in the column can be increased up to over 50 cm, which makes easier to increase the production scale, shortening the process time, further increasing the capacity of a single batch and reducing the costs.

Based on the old process, the present invention optimizes the chromatography resins and purification process of OsrHSA, so as it meets Chinese Pharmacopoeia and US Pharmacopoeia's requirements that the endotoxin contents lower than 0.0083 EU/mg OsrHSA, and ICH requirements of the residual HCPs contents as recombinant drugs, ensuring the safety of OsrHSA in clinical applications.

1. Screening of Chromatography Resins

In the old process, the chromatography resin was the agarose matrix, which is not pressure tolerable, a low flowing rate and limited filling height. These not only severely affects the isolation and purification efficiency, but also limits the overall binding capacity so that investment will be increased for numbers of the chromatography columns. In the new process, the resins with a rigid matrix were used in the second and third chromatography steps, which could increase the resin filling height, improve the isolation efficiency of OsrHSA and then increase the purity of recombinant human albumin. The main parameters between the new process and the old process is shown in Table 1. As shown in Table 1, comparison with the agarose matrix resin in chromatography A, the rigid matrix resin filling height in chromatography B and C is from 30 cm to 50 cm. As a results, loading volume of resin in column increased 66.7%.

TABLE 1

Chromatography resins for the new process and the old process

| | Old process | New process | Loading height |
|---|---|---|---|
| Chromatography A | BESTAROSE DIAMOND MMC ™ | BESTAROSE DIAMOND MMC ™ | 30 CM |
| Chromatography B | DIAMOND MMA ™ | UNIHAM-50 S ™ | 50 CM |
| Chromatography C | PHENYL BESTAROSE HP ™ | UNIHR PHENYL 30 L ™ | 50 CM |

2. Optimization of the Chromatography Parameters in the New Process

To optimize the sampling and elution parameters in the second chromatography step, the same batch samples from chromatography A was used. The critical quality parameters, including HCP content, OsrHSA purity, dimer content and endotoxin content in OsrHSA were studied using UNIHAM-50S™ resin in chromatography B. Under the elution condition of 10~20 mM PB, 150-300 mM NaCl, pH 7.0~8.0 and conductivity 15~35 mS/cm, the results are shown in Table 2. The pH of the elution buffer had a mini effect on the HCP content, while the conductivity of the elution buffer had a significant effect on the HCP content and recovery rate. The recovery rate and HCP content of recombinant human albumin are increased with the conductivity of the elution buffer increased, however, the purity is decreased accordingly. According to the results, the best HCP removal effects are the loading buffer with a pH of 8.0/a conductivity of 5 mS/cm, the washing buffer with a pH of 8.0/a conductivity of 9~9.5 mS/cm, a washing buffer volume of 12 CV and the elution buffer with a pH of 8.0 and a conductivity of 26.9 mS/cm.

TABLE 2

The design of optimization of HCP removal conditions in UNIHAM-50S ™ chromatography

| Experiment No. | Mode | pH | Cond (mS/cm) | HCP (μg/g) | Purity (%) | Recovery (mg) |
|---|---|---|---|---|---|---|
| 1 | +− | 7.99 | 15.58 | 174.9 | 100.0 | 94 |
| 2 | A0 | 8.01 | 25.40 | 135.9 | 98.9 | 277 |
| 3 | 0a | 7.50 | 15.40 | 192.0 | 99.4 | 101 |
| 4 | 00 | 7.50 | 24.90 | 127.2 | 98.5 | 310 |
| 5 | 0A | 7.49 | 35.15 | 137.0 | 94.9 | 384 |

TABLE 2-continued

The design of optimization of HCP removal conditions in UNIHAM-50S ™ chromatography

| Experiment No. | Mode | pH | Cond (mS/cm) | HCP (μg/g) | Purity (%) | Recovery (mg) |
|---|---|---|---|---|---|---|
| 6 | ++ | 8.00 | 35.12 | 128.2 | 95.2 | 381 |
| 7 | −+ | 7.01 | 35.10 | 149.7 | 94.0 | 363 |

Note:
+ presents high level point, − presents low level point, A presents axial point, 0 presents center point. For example, Design No. 1 refers to a mode of combination of high level point of pH and low level point of conductivity, noted as +−.

3. Effect on Dimer Content of the New Process (UNIHAM-50S™) and the Old Process (BESTAROSE DIAMOND MMA™)

In the old process, the endotoxin content was increased with the increase of dimer content. We compared the dimer content of the new process with that of the old process. The results showed that the endotoxin content was much lower than that in the old process. Unlike old process, endotoxin contents in new process did not increase with the increase of the dimer. The results indicated that the dimer content was mainly related to the conductivity of the elution buffer, i.e. as the conductivity increased with the dimer content increased. When the elution conductivity ranges from 40~47 mS/cm, the dimer contents in eluate could be controlled in the range of 2~7% (Table 3). Therefore, the conductivity of the elution buffer was 40~47 mS/cm, and preferably was 42 mS/cm in chromatography B of the new process.

TABLE 3

Content of dimer under different elution conditions

| | Filler | Batch No. | Elution conductivity (mS/cm) | Dimer (%) |
|---|---|---|---|---|
| Old process | BESTAROSE DIAMOND MMA ™ | 20211222-1 | 42.6 | 0.96 |
| New process | UNIHAM-50 S ™ | 20220514-1 | 27.1 | 0.27 |
| | | 20220517-1 | 32.1 | 0.29 |

TABLE 3-continued

Content of dimer under different elution conditions

| Filler | Batch No. | Elution conductivity (mS/cm) | Dimer (%) |
|---|---|---|---|
| | 20220627-2 | 41.2 | 2.99 |
| | 20220627-1 | 46.5 | 5.88 |

3. Effect on Endotoxin Content of Hydrophobic Chromatography Resin UniHR Phenyl in the New Process Lower endotoxin content is one of the key critical quality parameter for the clinical use of OsrHSA. In the old process, the PHENYL BESTAROSE HP™ was mainly used in chromatography C, in which step is to remove trace amounts of endotoxin from the previous BESTAROSE DIAMOND MMA™ chromatography step, although relatively good results was obtained. It was necessary to further reduce the endotoxin content ensuring more low endotoxin contents for more safer purpose. In the new process, a hydrophobic resin with rigid matrix, UNIHR PHENYL™ with particle sizes of 80 μm, 60 μm and 30 μm were used for comparison, respectively. Detail protocol are: the product II from the second chromatography B (batch 20220627-2) with endotoxin contents from 0.0417~0.0521 EU/mg was used this study. The product II was filtered and prepared with different loading conductivity (the chromatography buffer was 10~20 mM PB, 500~600 mM $(NH_4)_2SO_4$, 2 g/L sodium octanoate, between about pH 6.5 to 6.6), and then was loaded onto UNIHR PHENYL 80L™ UNIHR PHENYL 30L™ and UNIHR PHENYL 60S™, respectively. The results showed that the endotoxin content of the eluates in all treatments was less than 0.0083 EU/mg in the old process. Except for UNIHR PHENYL 80 L™, endotoxin contents was as low as 0.0004~0.0033 EU/mg. In particular, the endotoxin content was the lowest (0.0003~0.0013 EU/mg) when using UNIHR PHENYL 30L™ at the same conductivity (84 mS/cm), which was 6.3~27.6 fold lower than that of the old process (Table 4). The results showed that UNIHR PHENYL 30L™ with the elution conductivity was 80~92 mS/cm presented very good removal of trace residual endotoxin, and preferably 84 mS/cm.

TABLE 4

Removal of trace endotoxins by UNIHR PHENYL ™ resins with different particle sizes

| Fillers | Loading conductivity (mS/cm) | Endotoxin (EU/mg) |
|---|---|---|
| UNIHR PHENYL 80 L ™ | 80 | >0.0017 |
| | 84 | 0.0016~0.0033 |
| | 88 | 0.0004~0.0014 |
| | 92 | 0.0016~0.0033 |
| UNIHR PHENYL 30 L ™ | 80 | 0.0004~0.0014 |
| | 84 | 0.0003~0.0013 |
| | 88 | 0.0013~0.0028 |
| | 92 | 0.0016~0.0033 |
| Old process | 84 | 0.0083 |

4. Comparative Analysis of the HCP Content and Species Between the New Process and the Old Process As described above, the new process significantly reduced the endotoxin content. As the HCP content and species are critical to the safety of recombinant human serum albumin for clinical use, we compared the HCP contents and species between the new process and the old process. The results are shown in Table 5. The HCP contents in the old process and the new process was 0.64 μg/g and 0.60 μg/g, respectively, with no significant difference between the two processes, however, a significant difference in the HCP species is found. Total of 11 HCP species in the new process compared to 27 species in the old process, indicating that the safety was significantly improved.

TABLE 5

Comparison of the HCP content of the old process and the new process

| Process | Batch No. | HCP (μg/g)[A] | HC Pspieces[B] |
|---|---|---|---|
| Old process | C001201910003 | 0.60 | 27 |
| New process | 20220627-2 | 0.64 | 11 |

A: double antibody sandwich ELISA developed for rice host proteins was used to detect the host cell protein residues in the obtained stock solution. The HCP residues in the stock solution referred to the ratio of the detected concentration of host cell protein to the concentration of recombinant human serum albumin.

B: High resolution mass spectrometry (LC-MS/MS) was used to detect the total amount and species of host cell protein in the obtained stock solution.

3. Comparison of Chromatography Loading Capacity Between the New Process and the Old Process First chromatography step:

1) Preparation of loading-sample: The parameters of the extraction and the first chromatography step in the new process were the same as that of the old process.

700 Kg of rice flour was extracted and clarified and subjected to the first chromatography step. The collected eluate was added with pure water and a protective agent, adjusted to pH 8.0 and conductivity as 5.4 mS/cm, followed by aseptic filtration, and then used for chromatography on UNIHAM-50S.

2) secondary Chromatography step: UNIHAM-50S™ resin was filled into a 45 cm diameter chromatography column with a resin height of 48.8 cm. The chromatography was performed at a flow rate of 400~600 L/h. The buffer used for the chromatography sequentially comprises:

Equilibration buffer: 10~20 mM PB, pH 7.95~8.05, Cond 1~3 mS/cm;

Re-equilibration buffer: the same as the equilibration solution;

Wash buffer: 10~20 mM PB, 150~170 mM NaCl, pH 7.95~8.05, Cond 9~9.5 mS/cm;

Elution buffer: 10~20 mM PB, 420~460 mM NaCl, pH 7.95~8.05, Cond 41~43 mS/cm.

Third chromatography step:

1) Preparation of the sample: ammonium sulfate was added to the eluate from the UNIHAM-50S™ chromatography in the second step to prepare a stock solution adjusted to a pH of 6.57 and a conductivity of 84.34 mS/cm, followed by aseptic filtration, and then used for the third chromatography on UNIHR PHENYL 30L™.

2) Chromatography step: The UNIHR PHENYL 30L™ resin was filled into a 30 cm diameter chromatography column with a height of 44.2 cm and the chromatography was performed at a flow rate of between about 70 to 80L/h. The equilibration buffer used for the chromatography comprised 10~20 mM PB, 500~600 mM $(NH_4)_2SO_4$, 2 g/L sodium octanoate, pH 6.5~6.6.

In the new process, a nano-micro rigid resin was used in the second and third steps. The old process had a resin filled height of 30 cm for the agarose soft matrix, whereas the new process had a column filling height of 50 cm for the rigid matrix resin. As the column volume increased, the amount of the filled resin also increased. The resin volume and loading capacity of the second and third chromatography of the new process increased by a factor of 1.7, respectively, compared to the old process (Table 6).

TABLE 6

Comparison of column volume and loading capacity between the new process and the old process

| Process | Chromatography steps | Column height (cm) | Column diameter (cm) | Column volume (L) | Loading capacity (g/L) | Total loading capacity (g) |
|---|---|---|---|---|---|---|
| Old process | BESTAROSE DIAMOND HAM ™ | 30 | 100 | 230.5 | 23.6 | 5439.8 |
| | Phenyl Bestarose HP ™ | 30 | 100 | 230.5 | 45.9 | 10579.9 |
| New process | UNIHAM-50S ™ | 50 | 100 | 392.5 | 23.6 | 9263.0 |
| | UNIHR PHENYL 30L ™ | 50 | 100 | 392.5 | 45.9 | 18015.8 |

Example 2: Purity Detection of Recombinant Human Serum Albumin

An ELISA assay for HCP (host cell protein, HCP) quantitative analysis was used. The detail methods: the crude extract was obtained from the engineered rice flour using the extraction process. The total impurity components that prepared by removal of OsrHSA was used as the antigen to immunize rabbits to obtain an anti-impurity component serum. Then it was then purified by protein A and then the residual HSA antibodies was removed by the pHSA adsorption. The resulting purified antibody was used for HCP ELISA assay. The anti-total-impurity rabbit antibody as capture antibody was diluted 1:1000 in 50 mM, pH 9.6 carbonate buffer and added at 100 µL/well to a 96-well enzyme labeled plates and coated at 2~8° C. overnight. The plates were washed 5 times with 300 µL/well of PBS containing 0.05% Tween 20 (PBST), and blocked at room temperature for 2 hours after adding 300 µl/well of PBS containing 1% BSA. The plates were washed as above the steps, and then 0.5-100 ng/ml of anti-total-impurity antibodies diluted with 0.5% BSA-PBS (dilution buffer) was added to set as a standard curve. At the same time, the samples was diluted with the dilution buffer within the range of standard curve, and added to the blocked ELISA plates at 100 µL/well, incubated at room temperature for 2 hours. And then the plates were washed 5 times with PBST. Then biotin-labelled anti-total-impurity rabbit antibody with 1:5000 dilutions was added and incubated at room temperature for 1 hour. Then the plates were washed as above the steps. Horseradish peroxidase-labelled streptavidin with 1:20,000 dilution was added and incubated at room temperature under dark for 30 minutes. And then the plates were washed 10 times with PBST and patted dry. TMB was added at room temperature under dark for 20 minutes for color development. Finally 100 µL/well of 2 M sulphuric acid solution was added to terminate the color development. Values at 405 nm were measured using a microplate reader (Versamax, Molecular Device, USA). A standard curve was fitted with concentration against OD405 nm values by four-parameter model. The HCP concentration were back-calculated according to the absorbance values of the samples on the standard curve. The HCP contents in the OsrHSA samples were calculated according to standard curve.

The HCP contents of three consecutive batches of OsrHSA were detected by ELISA, and the detected data showed that the HCP content of the OsrHSA ranged from 0.5-0.6 µg/g protein. The OsrHSA purity was calculated to be more than 99.99994-99.99995% (Table 7).

TABLE 7

The HCP Content and the purity of OsrHSA

| Batch No. | C001201910003 | C001202009001 | C001202010002 |
|---|---|---|---|
| Host protein residue (µg/g) | 0.6 | 0.6 | 0.5 |
| Purity % | 99.99994 | 99.99994 | 99.99995 |

Purity calculation formula: % =

(total protein content − host cell protein content)/total protein content ∗ 100.

Example 3: Pyrogen Test of OsrHSA by a New Process

In order to further prove that the level of endotoxin does not produce pyrogen when used in human, the Rabbit Pyrogen Test (RPT) was performed according to the Chinese Pharmacopoeia. Detail methods: three rabbits were measured as normal body temperature, and then the rabbits were injected with protein (pre-warmed to 38° C.) at a dose of 0.6 g per 1 kg body weight within 15 min by slowly injected into the ear vein. The body temperature was measured every 30 minutes interval for 6 times. The highest of the six tested body temperatures minus the normal body temperature was the elevated temperature of the rabbit. After the administration of OsrHSA, the temperature of a single rabbit varied within the range of 0-0.1.1° C., and the total temperature increase of the three rabbits was less than 1.3° C. The results showed that OsrHSA with an endotoxin content lower than <0.0083 Eu/mg did not produce a febrile response in RPT (Table 8).

TABLE 8

Pyrogen test of OsrHSA in RPT

| Batch No. | C001201512001 | C001201512002 | C001201512003 |
|---|---|---|---|
| Maximum temperature rise in 3 rabbits ° C. | 0.4, 0.2, 0.5 | 0.0, 0.0, 0.1 | 0.0, 0.0, 0.0 |
| Maximum temperature drop in 3 rabbits ° C. | 0.0, 0.0, 0.0 | 0.0, −0.3, 0.0 | −0.5, −0.3, −0.2 |
| Total increase in body temperature of 3 rabbits | 1.1 | 0.1 | 0.0 |

Example 4: Detection of Residual DNA Content of OsrHSA

The residual host nucleic acid content of OsrHSA was detected using the method for the detection of residual DNA in rice of Chen et al. (Chen et al, Quantitation of the residual DNA from rice-derived recombinant human serum albumin. ANALYTICAL BIOCHEMISTRY, 2014, 450: 4-10). Detail methods: first, the test samples were appropriately diluted with DEPC (diethyl pyrocarbonate)-treated water; residual DNA was extracted from the diluted test samples using the WAKO DNA Extraction Kit (Wako Chemicals MSA, Richmond, VA, MSA). The rice genomic DNA as internal control was diluted as a standard template DNA solutions at concentrations of 1000 ng/ml, 500 ng/ml, 100 ng/ml, 10 ng/ml, 1 ng/ml, and 0.1 ng/ml, respectively. 5S rRNA gene from rice as internal reference (Chen et al. (2014)), a 40-cycle amplification assay was performed in a fluorescent quantitative PCR instrument by the SYBR Green method according to the following the primers, reaction parameters and amplification temperature. The standard curve was linearly fitted with Ct (y-axis) against the log standard template DNA concentration (x-axis), and the corresponding DNA concentration was back-calculated on the standard curve according to the Ct value of the residual DNA of the test samples. Then the residual DNA content of OsrHSA was calculated according to the re-solubilization volume of DNA and the initial dilution fold.

The results of the residual nucleic acid content of three consecutive batches of OsrHSA are shown in Table 9, and the residual nucleic acid content ranged from 0.01-0.002 ng/g.

TABLE 9

Residual host DNA content of recombinant human serum albumin

| | C001201910003 | C001202009001 | C001202010002 |
|---|---|---|---|
| Host DNA residues (ng/g) | 0.01 | 0.01 | 0.002 |

Example 5: Detection of Content and Types of Endotoxin from Plant-Derived Recombinant Human Serum Albumin Endotoxins are lipopolysaccharides (LPS) found in the outer membrane of Gram-negative bacteria. Residual endotoxins in biological agents may cause certain pathological reactions, such as endotoxemia (septic shock caused by severe immune responses). Recombinant biopharmaceuticals are therapeutic and preventive biological products produced using complex biological systems, such as rice endosperm cells, bacteria, yeast, virus or mammalian cells. Microbes may be introduced from materials, containers, equipment, production environment, personnel during the manufacturing processing of biopharmaceuticals, which would result in endotoxin contamination. The content and types of endotoxins in biopharmaceuticals depends on different expression systems, in which uses different culture media, fermentation control parameters, production environments etc. The lipopolysaccharide subunits of endotoxin are complex amphiphilic molecules with a molecular weight arranges from approximately 10-120 kDa. Due to the amphipathic and wide molecule mass of endotoxins, it is difficult to remove during downstream processing in term of binding to the proteins, particularly human serum albumin can bind the LPS. Furthermore, different expression systems used different host and culture conditions, the endotoxin types are totally different. Therefore, it is challenges to evaluate the endotoxins in different expression systems and different target proteins. Based on these characteristics, removal of the endotoxins in different expression systems also different because the endotoxins are highly diversity at different expression systems and target proteins.

To determine the endotoxin types of different expression systems, the commercially antibody against *E. coli* J5 LPS was used to detect endotoxin types from four expression systems used as hosts such as *E. coli*, rice endosperm cell, CHO-K1, and yeast.

5.1 Methods 5.1.1 SDS-Polyacrylamide Gel Electrophoresis (SDS-PAGE)

80 μl of extract supernatants from *Escherichia coli* lysate supernatant, CHO-K1 supernatant, yeast culture supernatant, and plant-derived recombinant human serum albumin were used for this study. Twenty μl 5× non-reducing Loading buffer were added to the samples, then were shaked and mixed. Five μl sample was loaded in the 15% PAGE gel. Then electrophoresis was operated with the voltage 160V for 50 minutes. After the electrophoresis, the PAGE was stained with protein stainer (Genscript, estain L1). The photograph was obtained.

5.1.2 Western Blotting (WB)

Electrophoresis was carried out described as 5.1.1. After electrophoresis, the proteins were transferred onto NC membrane using constant voltage of 100V for 45 minutes. The blotted membrane was put in an incubation box and rinse with PBST for 5 minutes and take out the solution, 10 ml of 5% BSA-PBST blocking solution was added into the box. Then incubated at room temperature for 40 minutes with shaking.

*E. coli* J5 LPS Monoclonal antibody (2D7/1, Invitrogen) antibody as primary antibody with 1000 dilution was added into 10 ml blocking solution. And then incubated at 4° C. for overnight. After the incubation, removed the solution, then add 20 ml PBST to rinse the NC membrane three times for 5 minutes each.

A Goat Anti-Rabbit IgG (H+L) AP (ZB2308) as secondary antibody with 5000 dilutions was added into 10 ml blocking solution and incubated at room temperature for 1 hour. After the incubation, remove the solution, then add 20 ml PBST to rinse the NC membrane three times for 5 minutes each. Add 100 μl 50 mg/ml NBT and 50 mg/ml BCIP into 15 ml AP color development solution (20 mM Tris, 20 mM NaCl, 20 mM MgCl2, pH9.5), respectively. Color development was carried out at room temperature in the dark for 3 hours. After the color-developed pictures are rinsed with purified water, they are photographed and saved with a camera.

5.2. Results

Figure 2:
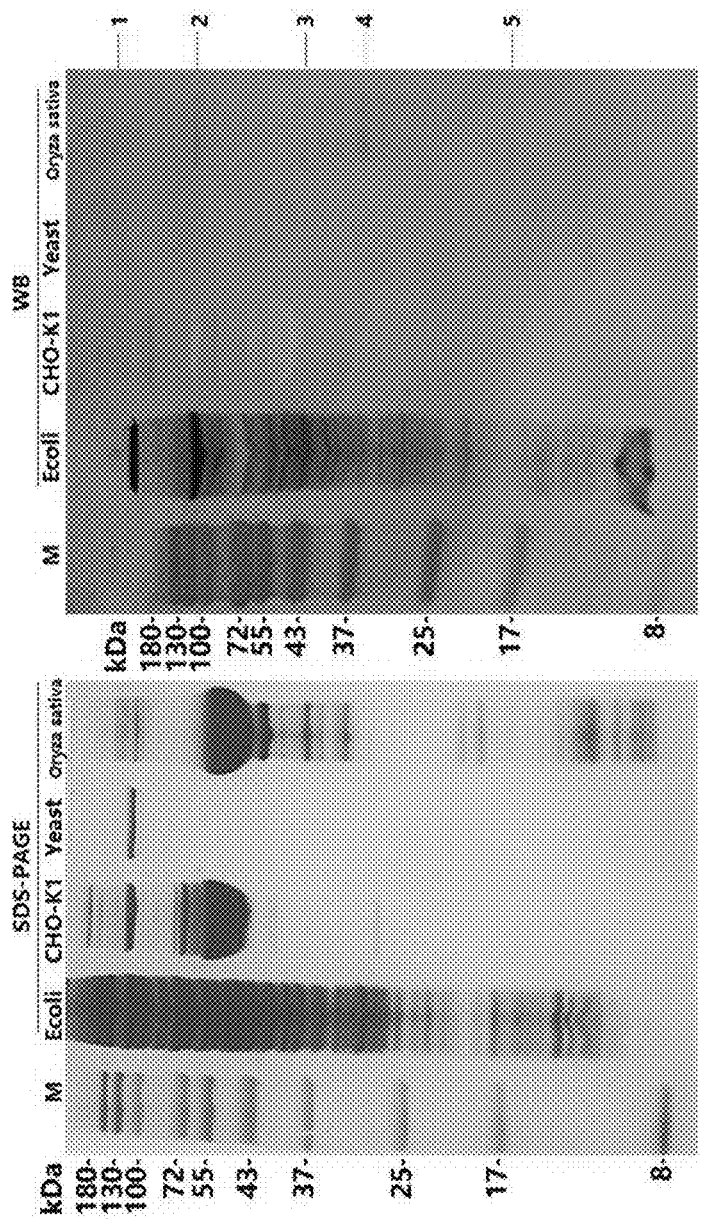
FIG. 2 illustrates an SDS-PAGE and WB analysis of endotoxin from different expression system

As shown in FIG. 2, the results indicated that profiles of molecular mass of endotoxins in different expression systems are significantly different. The widest band range and the widest molecular weight span was observed in *E. coli* expression system, ranges from 8 kDa to >180 kDa; Five main endotoxin components were observed in rice endosperm expression system, which are 8-25 kDa, 25-43 kDa and >180 kDa, respectively. Three main types of endotoxin were conserved in CHO-K1 expression system, arranging from 72-100 kDa and >180 kDa, respectively. Only one main endotoxin component was observed in yeast expression system, all distributed in in >180 kDa. These results demonstrated that the properties of endotoxins or endotoxin protein complexes are significant different among expression systems. The results showed that the total endotoxin contents in one expression system cannot be represented in another expression system. Due to the wide molecular mass ranges and the profiles of endotoxins in different expression systems are quite different, the removal of endotoxins from different expression systems should be different. Furthermore, the same expression system with different processing parameter could have different endotoxin profile. So, very different endotoxin removal methods or strategy will be used for different expression systems.

Example 6: Safety Assessment of High-Purity OsrHSA in Healthy Subjects

OsrHSA was prepared according to the method of the above Example 1.

A clinical phase I study to assess the safety and tolerability of OsrHSA was conducted in a healthy population. A total of 41 subjects were recruited and administered with OsrHSA and placebo at five cohorts of 20 mg/kg, 40 mg/kg, 80 mg/kg, 140 mg/kg and 200 mg/kg body weight, respectively. The results showed that no adverse events associated with OsrHSA (Table 11), no anti-drug antibodies (ADA) (Table 12) and no anti-HCP antibodies (Table 13) were reported during 30 days of follow-up after intravenous administration of OsrHSA.

TABLE 11

Adverse events of OsrHSA in healthy subjects

| Subject No. | Race | Dose Group | Dose | Type of Adverse Event | Severity | Drug Relevance |
|---|---|---|---|---|---|---|
| 005 | Non-Asian | Group 1 | Placebo | Headache | Slight | Not relevant |
| 045 | Non-Asian | Group 2 | 40 mg/kg | Common cold | Slight | Not relevant |
| 053 | Non-Asian | Group 2 | 40 mg/kg | Excessive stomach acid | Slight | Not relevant |
| 112 | Asian | Group 3 | 80 mg/kg | Sore throat | Slight | Not relevant |
| 149 | Non-Asian | Group 4 | 140 mg/kg | Dysmenorrhea | Slight | Not relevant |
| 173 | Asian | Group 4 | 140 mg/kg | Common cold | Slight | Not relevant |

TABLE 12

Detection of anti-drug antibody of OsrHSA in healthy subjects

| Visiting time | Placebo (N = 10) | OsrHSA | | | | |
| | | Group 1 20 mg/kg (N = 6) | Group 2 40 mg/kg (N = 6) | Group 3 80 mg/kg (N = 6) | Group 4 140 mg/kg (N = 7) | Group 5 200 mg/kg (N = 6) |
|---|---|---|---|---|---|---|
| Before administration | (—) | (—) | (—) | (—) | (—) | (—) |
| Day 8 | (—) | (—) | (—) | (—) | (—) | (—) |
| Day 15 | (—) | (—) | (—) | (—) | (—) | (—) |
| Day 20 | (—) | (—) | (—) | (—) | (—) | (—) |
| Day 30 | (—) | (—) | (—) | (—) | (—) | (—) |

TABLE 13

Detection of anti-HCP antibody of OsrHSA in healthy subjects

| | | | OsrHSA | | | | |
|---|---|---|---|---|---|---|---|
| Visiting time | Results | Placebo (N = 10) | Group 1 20 mg/kg (N = 6) | Group 2 40 mg/kg (N = 6) | Group 3 80 mg/kg (N = 6) | Group 4 140 mg/kg (N = 7) | Group 5 200 mg/kg (N = 6) |
| Before administration | Positive | 1 (10.00%) | 0 (0.00%) | 0 (0.00%) | 0 (0.00%) | 1 (14.29%) | 1 (16.67%) |
| | Negative | 9 (90.00%) | 6 (100.0%) | 6 (100.0%) | 6 (100.0%) | 6 (85.71%) | 5 (83.33%) |
| Day 8 | Positive | 1 (10.00%) | 0 (0.00%) | 0 (0.00%) | 0 (0.00%) | 1 (14.29%) | 1 (16.67%) |
| | Negative | 9 (90.00%) | 6 (0.0%) | 6 (100.0%) | 6 (100.0%) | 6 (85.71%) | 5 (83.33%) |
| Day 15 | Positive | 1 (10.00%) | 0 (0.00%) | 0 (0.00%) | 0 (0.00%) | 1 (14.29%) | 1 (16.67%) |
| | Negative | 8 (80.00%) | 5 (83.33%) | 6 (100.0%) | 6 (100.0%) | 6 (85.71%) | 5 (83.33%) |
| Day 22 | Positive | 1 (10.00%) | 0 (0.00%) | 0 (0.00%) | 0 (0.00%) | 1 (14.29%) | 1 (16.67%) |
| | Negative | 8 (80.00%) | 4 (66.67%) | 6 (100.0%) | 6 (100.0%) | 6 (85.71%) | 4 (66.67%) |
| Day 30 | Positive | 1 (10.00%) | 0 (0.00%) | 0 (0.00%) | 0 (0.00%) | 1 (14.29%) | 1 (16.67%) |
| | Negative | 8 (80.00%) | 5 (83.33%) | 6 (100.0%) | 6 (100.0%) | 6 (85.71%) | 4 (66.67%) |

In summary, OsrHSA is safe and well tolerant; no anti-drug antibodies (ADA) and no anti-HCP antibodies in all subjects were found after the administration.

Example 7: Immunogenicity of High-Purity OsrHSA in Cirrhotic Ascites Patients

High-purity OsrHSA was prepared according to the method of the above Example 1.

A phase II clinical study was conducted in patients with cirrhotic hypoproteinemia. ADA and anti-HCP antibody were detected before and after administration in a total of 220 patients aged 18~80 years with decompensated cirrhosis combined with ascites whose serum albumin concentration was less than or equal to 30 g/L. High-purity OsrHSA was intravenously administered 10 and 20 g/day for 14 consecutive days with a 30-day follow-up, respectively. ADA were detected at 7, 15 and 30 days after the completion of administration, respectively. The results showed that no clinically significant ADA were observed in 176 patients with cirrhosis treated with OsrHSA (Table 14). No clinically significant anti-HCP antibodies were detected after treatment with OsrHSA in all patients (Table 15).

The results of the two studies of US-HY1001 and US-China-HY1001, it was concluded that OsrHSA is no immunogenicity and low immunogenicity of HCP, indicating OsrHSA has safety.

TABLE 14

Incidence of ADA in each dose group after treatment with OsrHSA

| | OsrHSA 10 g (N = 85) n (%) | pHSA 10 g (N = 22) n (%) | OsrHSA 20 g (N = 86) n (%) | pHSA 20 g (N = 23) n (%) |
|---|---|---|---|---|
| Positive at baseline - still positive after treatment | 1 (1.2) | 0 (0.0) | 0 (0.0) | 0 (0.0) |
| Negative at baseline - positive after treatment | 2 (2.4) | 0 (0.0) | 0 (0.0) | 0 (0.0) |
| 1-5 fold increase in antibody titre after treatment | 3 (3.5) | 1 (4.5) | 6 (7.0) | 0 (0.0) |
| 6-10 fold increase in antibody titre after treatment | 0 (0.0) | 0 (0.0) | 0 (0.0) | 0 (0.0) |
| >10-fold increase in antibody titre after treatment | 0 (0.0) | 0 (0.0) | 0 (0.0) | 0 (0.0) |

Note:
N = number of participants in the treatment group for the analysis set, N = number of participants in the relevant category in the treatment group. pHSA is plasma-derived human serum albumin.

TABLE 15

Incidence of ADA in each dose group after treatment with OsrHSA

| | OsrHSA 10 g (N = 85) n (%) | pHSA 10 g (N = 22) n (%) | OsrHSA 20 g (N = 86) n (%) | pHSA 20 g (N = 23) n (%) |
|---|---|---|---|---|
| Positive at baseline - still positive after treatment | 12 (14.1) | 4 (18.2) | 11 (12.8) | 5 (21.7) |
| Negative at baseline - positive after treatment | 0 (0.0) | 1 (4.5) | 0 (0.0) | 0 (0.0) |
| 1-5 fold increase in antibody titre after treatment | 10 (11.8) | 4 (18.2) | 7 (8.1) | 6 (26.1) |

TABLE 15-continued

Incidence of ADA in each dose group after treatment with OsrHSA

|  | OsrHSA 10 g (N = 85) n (%) | pHSA 10 g (N = 22) n (%) | OsrHSA 20 g (N = 86) n (%) | pHSA 20 g (N = 23) n (%) |
|---|---|---|---|---|
| 6-10 fold increase in antibody titre after treatment | 0 (0.0) | 0 (0.0) | 0 (0.0) | 0 (0.0) |

Note:
N = number of participants in the treatment group for the analysis set, n = number of participants in the relevant category in the treatment group.

Example 8: Efficacy of High-Purity OsrHSA in Cirrhotic Ascites Patients

OsrHSA was intravenously administered to the patients with cirrhotic ascites hypoproteinemia whose human serum albumin levels were below 30 g/L with 10 g or 20 g/day for 14 consecutive days. The primary endpoints is the days reached to over 35 g/L. Plasma-derived human serum albumin (pHSA) was used as positive control. The statistical analysis was performed using the full analysis set (FAS) approach. The statistical analysis indicated that OsrHSA is non-interfior to pHSA at a 10 g dose (lower limit of 97.5% CI=−0.114) and 20 g doses (lower limit of 97.5% CI=−0.187). Both reached the primary endpoint setting of level of criteria of non-interfior −0.20. The statistical analysis was performed using a per-protocol analysis set (PPAS) approach. The results indicated that OsrHSA is non-inferior to the pHSA at both the 10 g (lower limit of 97.5% CI=−0.076) and 20 g (lower limit of 97.5% CI=−0.106) dose levels. When all two dose levels were analyzed, the efficacy of OsrHSA was non-inferior to pHSA in the FAS (lower limit of 97.5% CI=−0.119) and PPAS (lower limit of 97.5% CI=0.065) populations (Table 16). The median value of days reached greater than or equal to (≥) 35 g/L serum albumin level is 9 days (OsrHSA) and 12 days (pHSA) at 10 g dose group, OsrHSA is 3 days earlier than that of pHSA. The median value of days reached ≥35 g/L serum albumin level is 6 days at both OsrHSA and pHSA at 20 g dose group.

TABLE 16

Analysis of the primary endpoints of OsrHSA

| Queue | Analysis set | OsrHSA n/N (%) | pHSA n/N (%) | Rate difference | 97.5% CI lower limit |
|---|---|---|---|---|---|
| 20 g | FAS | 72/86 (0.837) | 21/23 (0.913) | −0.076 | −0.187 |
|  | PPS | 72/77 (0.935) | 21/22 (0.955) | −0.020 | −0.106 |
| 10 g | FAS | 58/85 (0.682) | 13/22 (0.591) | 0.091 | −0.114 |
|  | PPS | 57/79 (0.722) | 13/22 (0.591) | 0.131 | −0.076 |
| Combined analysis | FAS | 130/171 (0.760) | 34/45 (0.756) | 0.005 | −0.119 |
|  | PPS | 129/156 (0.827) | 34/44 (0.773) | 0.054 | −0.065 |

Note:
FAS = full analysis set, PPS = per-protocol set.

Example 9: Application of High-Purity OsrHSA in Pharmaceutical Excipients

Recombinant reteplase from *Oryza sativa* (OsrPA) was prepared described in CN202110735731.0.

High-purity OsrHSA was prepared according to the method of the above Example 1.

HSA is also usually used as a freeze-drying protectant/excipient in the pharmaceutical formulations. High-purity OsrHSA can be used as an excipient of pharmaceuticals, which has a protective function on enzyme/antibody drugs as well as an excipient effect. The morphology and bioactivity of OsrPA were investigated using different protectants.

TABLE 17

Stability of OsrPA formulations using OsrHSA at 6-month accelerated stability study

| Test items | Acceptance criteria | Batch No. | Accelerated stability (25 ± 2° C., RH60% ± 5%)/month | | | | |
|---|---|---|---|---|---|---|---|
|  |  |  | 0 | 1 | 2 | 3 | 6 |
| SEC-HPLC purity | monomer ≥96.0% | C036202109003 | 99.5 | 97.6 | 98.6 | 98.8 | 98.4 |
|  |  | C036202109004 | 99.0 | 98.1 | 98.4 | 98.8 | 98.5 |
|  |  | C036202109005 | 98.4 | 97.8 | 98.5 | 98.9 | 98.5 |
| OsrPA protein content | should be 10.0-14.0 mg/vial | C036202109003 | 13.0 | 13.2 | 12.0 | 11.8 | 10.2 |
|  |  | C036202109004 | 13.0 | 12.5 | 13.3 | 11.6 | 10.7 |
|  |  | C036202109005 | 11.0 | 11.8 | 10.8 | 11.9 | 11.1 |
| Biological | should be | C036202109003 | 112.8 | 109.6 | 103.7 | 101.0 | 98.0 |

TABLE 17-continued

Stability of OsrPA formulations using OsrHSA at 6-month accelerated stability study

| Test items | Acceptance criteria | Batch No. | Accelerated stability (25 ± 2° C., RH60% ± 5%)/month | | | | |
|---|---|---|---|---|---|---|---|
| | | | 0 | 1 | 2 | 3 | 6 |
| activity | 90.0%~120.0 % of labeled amount (5 million U/vial) | C036202109004 | 105.7 | 105.1 | 102.2 | 100.5 | 107.7 |
| | | C036202109005 | 95.2 | 101.6 | 102.2 | 99.4 | 105.7 |

Three consecutive batches of OsrPA drug product formulations containing OsrHSA were performed for accelerated stability studies. The results showed that the OsrPA met the quantity criteria of the purity, moisture content (2.1%) and bioactivity after 6 months of acceleration test (Table 17). The results indicated OsrHSA as of protectant for OsrPA drug was the best effects over other protectants.

A number of embodiments of the invention have been described. Nevertheless, it can be understood that various modifications may be made without departing from the spirit and scope of the invention. Accordingly, other embodiments are within the scope of the following claims.

What is claimed is:

1. A method for preparing high-purity recombinant human serum albumin from *Oryza sativa* (OsrHSA), comprising the following steps of:
   (a) preparing a crude or unpurified extract of OsrHSA;
   (b) subjecting the crude extract of OsrHSA to cation exchange chromatography (A) comprising a cation exchange column, whereby OsrHSA binds to the cation exchange column,
   (c) providing:
   a first washing buffer comprising between about 10-20% absolute isopropanol by volume,
   an equilibration buffer I comprising between about 0-10% absolute isopropanol by volume, and
   an equilibration buffer II comprising between about 5-15% absolute isopropanol by volume,
   (d) washing the cation exchange column with the first washing buffer, then washing the column with equilibration buffer I, then washing the column with equilibration buffer II,
   (e) eluting OsrHSA from the cation exchange chromatography, thereby obtaining a primary product I;
   wherein the cation exchange chromatography comprises a cationic/hydrophobic composite resin;
   (f) subjecting the primary product I to anion exchange chromatography B comprising an anion exchange column, to obtain an intermediate product II,
   wherein the anion exchange chromatography B comprises a composite resin-comprising a matrix having a pore size of about 60 μm and a flow rate of between about 150-750 cm/h;
   and the parameters of the anion exchange chromatography B comprise:
      (i) adding or loading onto to the anion exchange column a loading sample under conditions comprising: pH 8.0, conductivity between about 1 to 5 mS/cm;
      (ii) adding or loading onto to the anion exchange column a washing buffer under conditions comprising: pH 8.0, conductivity between about 9 to 9.5 mS/cm;
      (iii) adding or loading onto to the anion exchange column an elution buffer comprising: pH 8.0, conductivity between about 30 to 50 mS/cm;
      thereby eluting off the anion exchange column the intermediate product II,
   wherein the anion exchange chromatography B comprising an anion exchange column comprises use of the following buffers:
      an equilibration buffer comprising: between about 10 to 20 mM phosphate buffer (PB), between about 7.9 to 8.1 pH, conductivity between about 1 to 3 mS/cm;
      a re-equilibration buffer comprising: the same as the equilibration buffer;
      a second washing buffer comprising: between about 10 to 20 mM PB, between about 150 to 170 mM NaCl, between about 7.9 to 8.1, between about 9 to 9.5 mS/cm conductivity;
      an elution buffer comprising: between about 10 to 20 mM PB, between about 420 to 460 mM NaCl, between about pH 7.9 to 8.1, between about 41 to 43 mS/cm conductivity; and
   (g) subjecting the intermediate product II to hydrophobic chromatography (C) comprising loading the intermediate product II in a chromatography buffer onto a hydrophobic column,
   washing the hydrophobic column by loading the second washing buffer onto the hydrophobic column, and
   eluting the high-purity OsrHSA by loading an eluting buffer onto the hydrophobic column, thereby generating the high-purity OsrHSA,
   and the hydrophobic chromatography comprises use of a hydrophobic resin.

2. The method according to claim 1, wherein the OsrHSA is expressed in rice seed.

3. The method according to claim 1, wherein the elution buffer in the step (f) has a conductivity of between about 40 mS/cm and 47 mS/cm, or about 42 mS/cm.

4. The method according to claim 1, wherein the hydrophobic chromatography resin in the step (g) comprises highly crosslinked polymethacrylate beads of uniformed particle size and open pore structure.

5. The method according to claim 3, wherein the elution conductivity of the chromatography in the step (g) is between about 80-92 mS/cm.

6. The method according to claim 4, wherein the elution conductivity of the chromatography in the step (g) is between about 75 to 90 mS/cm or about 84 mS/cm.

7. The method according to claim 1, wherein the chromatography buffer used in step (g) comprises: between about 10 to 20 mM PB, between about 500 to 600 mM $(NH_4)_2SO_4$, between about 1 and 3 g/L, or about 2 g/L sodium octanoate, between about pH 6.5 to 6.6.

8. The method of claim 6, wherein the elution conductivity of the chromatography in the step (g) is between about 80 to 87 mS/cm.

9. The method of claim 4, wherein the crosslinked polymethacrylate beads have a particle size of about 35 μm and a pore size of about 500 μm.

10. The method of claim 4, wherein the hydrophobic chromatography resin in the step (g) has a dynamic binding capacity of about 30 mg/ml (Lys).

11. The method of claim 4, wherein the hydrophobic chromatography resin in the step (g) has an operating pressure of less than about 0.8M Pa and an operating pH range of between about pH 2 to pH 12.

12. The method of claim 1, wherein the hydrophobic chromatography comprises use of a rigid, hydrophobic resin.

13. A method for preparing high-purity recombinant human serum albumin from *Oryza sativa* (OsrHSA), comprising the following steps of:
(a) preparing a crude or unpurified extract of OsrHSA;
(b) subjecting the crude extract of OsrHSA to cation exchange chromatography (A) comprising a cation exchange column, whereby OsrHSA binds to the cation exchange column,
(c) providing:
a first washing buffer comprising between about 10-20% absolute isopropanol by volume,
an equilibration buffer I comprising between about 0-10% absolute isopropanol by volume, and
an equilibration buffer II comprising between about 5-15% absolute isopropanol by volume,
(d) washing the cation exchange column with the first washing buffer, then washing the column with equilibration buffer I, then washing the column with equilibration buffer II,
(e) eluting OsrHSA from the cation exchange chromatography, thereby obtaining a primary product I;
wherein the cation exchange chromatography comprises a cationic/hydrophobic composite resin;
(f) subjecting the primary product I to anion exchange chromatography B comprising an anion exchange column, to obtain an intermediate product II,
and the parameters of the anion exchange chromatography B comprise:
(i) adding or loading onto to the anion exchange column a loading sample under conditions comprising: pH 8.0, conductivity between about 1 to 5 mS/cm;
(ii) adding or loading onto to the anion exchange column a washing buffer under conditions comprising: pH 8.0, conductivity between about 9 to 9.5 mS/cm;
(iii) adding or loading onto to the anion exchange column an elution buffer comprising: pH 8.0, conductivity between about 30 to 50 mS/cm;
thereby eluting off the anion exchange column the intermediate product II,
wherein the anion exchange chromatography B comprising an anion exchange column comprises use of the following buffers:
an equilibration buffer comprising: between about 10 to 20 mM phosphate buffer (PB), between about 7.9 to 8.1 pH, conductivity between about 1 to 3 mS/cm;
a re-equilibration buffer comprising: the same as the equilibration buffer;
a second washing buffer comprising: between about 10 to 20 mM PB, between about 150 to 170 mM NaCl, between about 7.9 to 8.1, between about 9 to 9.5 mS/cm conductivity;
an elution buffer comprising: between about 10 to 20 mM PB, between about 420 to 460 mM NaCl, between about pH 7.9 to 8.1, between about 41 to 43 mS/cm conductivity; and
(g) subjecting the intermediate product II to hydrophobic chromatography (C) comprising use of a hydrophobic column to obtain the high-purity OsrHSA, comprising:
loading the intermediate product II onto the hydrophobic column in a buffer comprising between about 10 to 20 mM PB, between about 500 to 600 mM $(NH_4)_2SO_4$, between about 1 and 3 g/L, or about 2 g/L sodium octanoate, between about pH 6.5 to 6.6,
washing the hydrophobic column by loading the second washing buffer onto the hydrophobic column,
and eluting high-purity OsrHSA from the hydrophobic column by loading an eluting buffer onto the hydrophobic column, thereby generating the high-purity OsrHSA,
and the hydrophobic chromatography uses a hydrophobic resin.

14. The method of claim 13, wherein the hydrophobic chromatography comprises use of a rigid, hydrophobic resin.

* * * * *